United States Patent [19]

Blake, III

[11] Patent Number: 5,339,830
[45] Date of Patent: Aug. 23, 1994

[54] BLOOD COAGULATION TEST SYSTEM

[76] Inventor: Joseph W. Blake, III, 9 Taylor Ave., Norwalk, Conn. 06854

[21] Appl. No.: 822,724

[22] Filed: Jan. 21, 1992

[51] Int. Cl.⁵ .................. A61B 5/00; G01N 33/00
[52] U.S. Cl. .................... 128/771; 128/638; 422/73; 422/82.13; 436/69; 73/64.41; 604/211; 604/224
[58] Field of Search ............ 422/73, 82.13, 68.1; 436/69, 70; 73/64.41; 128/638, 771; 604/211, 224

[56] References Cited

U.S. PATENT DOCUMENTS

| | | | |
|---|---|---|---|
| 3,701,434 | 10/1972 | Moore | 210/477 |
| 3,963,349 | 6/1976 | Albright et al. | 422/64 X |
| 4,034,601 | 7/1977 | Geiger | 422/73 X |
| 4,434,802 | 3/1984 | Rilliet | 128/764 |
| 4,604,894 | 8/1986 | Kratzer et al. | 436/69 X |
| 4,780,418 | 10/1988 | Kratzer | 422/73 X |
| 4,810,249 | 3/1989 | Haber et al. | 604/211 X |
| 4,863,072 | 9/1989 | Perler | 604/224 X |
| 4,919,121 | 4/1990 | Rydell et al. | 604/97 |
| 5,047,015 | 9/1991 | Foote et al. | 604/224 X |
| 5,047,211 | 9/1991 | Sloane, Jr. et al. | 436/70 X |
| 5,051,239 | 9/1991 | von der Goltz | 422/73 |

FOREIGN PATENT DOCUMENTS

0129425  12/1984  European Pat. Off. .
8802116   3/1988  PCT Int'l Appl. .

Primary Examiner—Lyle A. Alexander
Assistant Examiner—Maureen M. Wallenhorst
Attorney, Agent, or Firm—Patrick J. Walsh

[57] ABSTRACT

A blood coagulation test system for in vitro assessment of blood characteristics including hemostasis, thrombus formation, thrombolysis, and collagen platelet interaction includes a syringe/test cartridge for collection, testing and disposal of the sample together with a test analyser for executing the test protocol. Coagulation functions are evaluated by establishing controlled bleeding of the sample from a capillary tube within the cartridge and monitoring these blood characteristics as a function of blood pressure variations occurring in the cartridge as the test proceeds. The blood sample remains within the cartridge for testing and after disposal.

36 Claims, 4 Drawing Sheets

BLOOD COAGULATION TEST SYSTEM

BACKGROUND OF THE INVENTION

The present invention relates to blood coagulation tests and particularly to such tests performed in vitro.

It is desirable to assess and monitor blood characteristics including hemostasis (cessation of venous or arterial bleeding), clotting or thrombus formation, and thrombolysis (dissolving clots in the blood stream) for a variety of medical procedures as for example treating blood disorders such as hemophilia, performing surgery, and blood transfusions. Such blood assessments are required promptly for surgical procedures, emergency room treatments, or blood transfusions and must be performed without the benefit of laboratory test conditions. In addition, aging and handling of a blood sample have significant effect on the blood clotting mechanism. Therefore it is necessary to provide a simple, on-site technique for in vitro assessment of blood characteristics as soon as practicable after a blood sample is drawn. The technique must also provide reliable, reproducible results.

European Patent Application No 84/304055.1 dated Jun. 15, 1984, PCT International Application No PCT/GB87/00633 and U.S. Pat. No. 5,047,211 disclose techniques for in vitro assessment of blood specimens. In those techniques, a blood sample is placed in a reservoir or container and passed through a capillary tube into a waste collection container. Blood flow through the tube is established under constant pressure (60 mm Hg), temperature (37 deg. C.) and flow rate simulating venous conditions. The capillary tube is punctured to establish bleeding and to allow for hemostasis to occur, i.e., the formation of a platelet plug in the tube puncture and cessation of bleeding. Blood pressure in the tube drops when the puncture occurs and rises gradually as the platelet plug forms in the puncture opening. The time required for full pressure recovery is observed and provides an index of the hemostasis characteristic of the blood sample. By placing a fragment of collagen (catgut, for example) in the tube the platelet collagen interaction can be assessed for a native (non anti-coagulated) blood sample.

Those patent documents reveal a number of measures and precautions taken to assure reliability and repeatability of blood assessment results, and to assure that in vitro conditions conform as nearly as possible to in vivo.

Manipulation of the blood sample must be held to a minimum because agitation or turbulence of the sample between patient and test reservoir as, for example, by transferring the sample from a collection syringe to a test reservoir, can cause release of ADP (adenosine diphasphate) in the sample and initiate the clotting-/hemostasis process. Pumping the blood causes severe damage to corpuscles and inconsistent results. On the other hand, as noted in EPO application '055, the blood sample must not be allowed to settle in a test reservoir because settling of blood solids effects hemostasis. Accordingly, the blood collecting container is used as the sample reservoir to minimize sample manipulation and turbulence. Additionally, the sample in the reservoir is stirred and pressurized by introducing a blood-immiscible hydrocarbon oil (paraffin) into the bottom of the reservoir. The paraffin oil is supplied under pressure for gently stirring the sample and for simulating in vivo pressure of 60 mm Hg in the reservoir and capillary tube of the test apparatus. The PCT patent document discloses an elaborate pressure regulator apparatus for assuring that constant pressure is applied to the test reservoir and capillary tube through the paraffin supply line.

In carrying out sample assessment, it is necessary to establish a steady flow rate of the sample through the capillary tube in order to determine a pressure datum for observing the hemostasis characteristic. Accordingly, the waste receptacle is filled with paraffin so that waste blood entering the receptacle via the capillary tube displaces a like volume of paraffin in order to maintain a constant back pressure and a steady flow rate through the capillary tube. A pressure transducer fitted to the waste receptacle measures pressure variations in the system and particularly in the tube. When blood flow is established and a pressure datum recorded at a value of 60 mm Hg, the tube is ready to be punctured.

In order to achieve repeatable blood assessment results, it is necessary for the test apparatus to puncture the capillary tube with a hole of constant size each time a blood test is performed. Therefore, puncture needle size and tube size must be standardized. In addition, the tube as well as needle must be precisely positioned and firmly held when puncture occurs. Any variation in hole geometry or contour will effect pressure measurements as well as the formation of a platelet plug in the capillary tube during hemostasis.

The capillary tube in the vicinity of the puncture is continually washed by a saline solution so that blood dripping and collecting outside the tube hole does not contribute to platelet plug formation. Accordingly the disclosed patent apparatus is provided with a saline wash system for cleansing waste blood from the exterior of the capillary tube in the vicinity of the puncture. The USA and PCT patent documents provide parallel test channels so that hemostasis, thrombolysis and collegen platelet interaction assessments can be performed at the same time. This parallel facility does require duplication of the assessing apparatus for each of the test channels.

Bloods specimens can communicate contagious diseases and they must be safely discarded. The disclosed patent techniques require disposal of the blood specimen together with contaminated paraffin, saline solution, punctured tubing, piercing needles, syringes and so forth. The '211 patent provides for disposal of an entire cassette embodying parallel channels for performing blood assessments. The spent blood sample, saline solution and paraffin are discarded along with the casette.

In summary, apparatus for accurate and repeatable in vitro assessment of blood characteristics must minimize manipulation, agitation, and mechanical stress of the sample; not allow the sample to settle in its collection reservoir; establish venous or arterial conditions of pressure, temperature, and flow rate; assess a blood sample as soon as possible after collection; provide a precise capillary tube aperture; and provide safe disposal of waste blood and contaminated components.

SUMMARY OF THE INVENTION

The present invention is directed to a system for assessment of blood coagulation characteristics. The system includes a cartridge for collecting, assessing, and disposing of a blood sample. Hemostasis, clot formation, thrombolysis, and platelet collagen interaction properties of a set of blood samples drawn from a patient may be evaluated. The system further includes a test analyser for receiving the cartridge and for performing tests on individual sample cartridges.

The test cartridge comprises a syringe-like instrument having an open ended cylindrical collection chamber and a collection plunger telescoped into the collection chamber. The telescoping portion of the plunger is provided with an external screw thread cooperating with a drive sleeve affixed around the collection chamber so that by rotating the sleeve the plunger is withdrawn from the chamber at a steady linear velocity when a blood sample is collected.

The collection plunger is divided longitudinally by a lateral bulkhead into a forward bleeding receptacle and an aft waste compartment. A capillary tube opens through the bulkhead and extends longitudinally forward through the bleeding receptacle and therebeyond opening into the sample collection chamber for conducting the blood sample through the cartridge. The tube is provided with a bleeding hole or aperture opening into the bleeding receptacle for determining hemostasis. The aperture is formed during manufacture of the test cartridge and its dimensions and contour are precisely controlled.

The aft waste compartment is occupied by a telescoping pressure piston slidably mounted therein for establishing and maintaining a control pressure during testing.

The invention further provides a test analyser for monitoring and recording blood characteristics. The analyser provides a heated environment for preheating cartridges to operating (body) temperature prior to drawing a blood sample and for maintaining a constant temperature during blood evaluation. The analyser also contains a drive mechanism for turning the test cartridge drive sleeve so as to telescope the plunger into the collection chamber in order to establish blood flow through the capillary tube at constant pressure and flow rate. The analyser provides a counterpressure on the rear control piston so that, together with a pressure sensor at the collection chamber inlet, the gradual buildup of pressure within the capillary tube is monitored and recorded as platelet plug formation occurs in the tube aperture.

In operation of the cartridge, a blood sample is drawn into the collection chamber by manually rotating the drive sleeve and moving the collection plunger rearward. Thereafter, the cartridge is fitted with a pressure diaphragm cap and is then placed in the test analyser and pressurized to establish blood flow through the capillary tube under controlled conditions of pressure, temperature and flow rate. The test analyser engages and rotates the drive sleeve thereby returning the plunger at a steady rate into the collection chamber so blood flows into the capillary tube to begin bleeding through the tube aperture into the bleeding receptacle. Blood flow continues along the tube through the dividing bulkhead and into the waste compartment. Blood entering the waste compartment remains under system pressure and moves the sliding control pressure piston backward in order to accommodate waste blood in the compartment.

The test analyser applies a counterpressure to the control piston in order to maintain a constant blood pressure within the capillary tube so that a platelet plug forms in the tube aperture under conditions simulating in vivo.

A pressure sensor at the inlet to the collection chamber enables the test analyser to monitor and record the gradual buildup of tube pressure as the platelet plug is formed. The pressure reading provides an index of hemostasis and the test is complete when hemostasis occurs.

After the hemostasis test is completed, the cartridge may be removed from the test analyser, and the cartridge properly capped and containing the entire waste blood sample may be discarded.

If desired, the same test cartridge and the test analyser may be used to evaluate thrombus formation and thrombolysis of the blood sample. A separate cartridge containing a separate blood sample may be used with the test analyser to evaluate collagen platelet interaction.

According to the invention, in vitro blood analysis is performed reliably and repeatably immediately after sample collection under test conditions of constant temperature, pressure, and flow rate with minimal manipulation, agitation, and mechanical stress of the sample and without the use and disposal of supplies and related apparatus for stirring agents such as paraffin and cleaning agents such as saline solution. Bleeding aperture geometry is precisely controlled for achieving test repeatability and reliability. Disposal is limited to test cartridge entirely containing the waste blood sample.

OBJECTS OF THE INVENTION

It is an object of the invention to provide a system for in vitro assessment of blood properties including hemostasis, clotting or thrombus formation, thrombolysis, and collagen platelet interaction.

Another object of the invention is to provide a test cartridge for drawing a blood sample at an even rate to minimize the possibility of platelet activation.

It is an object of the invention to provide a totally contained syringe/test cartridge for blood assessment which entirely contains a blood sample from collection through evaluation and disposal thereby eliminating transfer of the blood sample and attendent agitation or tubulence in the sample.

Another object of the invention is to provide a test cartridge which will accept a hypodermic needle, intravenous tube, and a combined pressure diaphragm and disposal cap.

It is a further object of the invention to provide a test analyser in cooperation with a test cartridge in which blood assessment is performed under conditions of constant temperature, pressure and flow rate.

It is a further object of the invention to provide a system for evaluating blood properties immediately after collection of a blood sample.

It is a further object of the invention to provide a system for analysing blood characteristics in vitro without the need to transfer a sample and with minimal manipulation, agitation, or mechanical stress of the sample.

Another object of the invention is to provide a test cartridge with a preformed hole in the bleeding tube to eliminate the requirement for puncturing the capillary tube during performance of a blood test.

It is a further object of the invention to provide a test system for blood analysis where extraneous materials and related apparatus for pressuring, stirring, and cleaning operations are not required.

Another object of the invention is to provide a syringe/test cartridge having a pressure diaphragm cap placed over the cartridge inlet after filling so that no blood contacts the test analyser during test performance.

It is another object of the invention to provide a test system for blood analysis with minimal disposal requirements.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which.

DETAILED DESCRIPTION OF THE INVENTION

Figure 1:
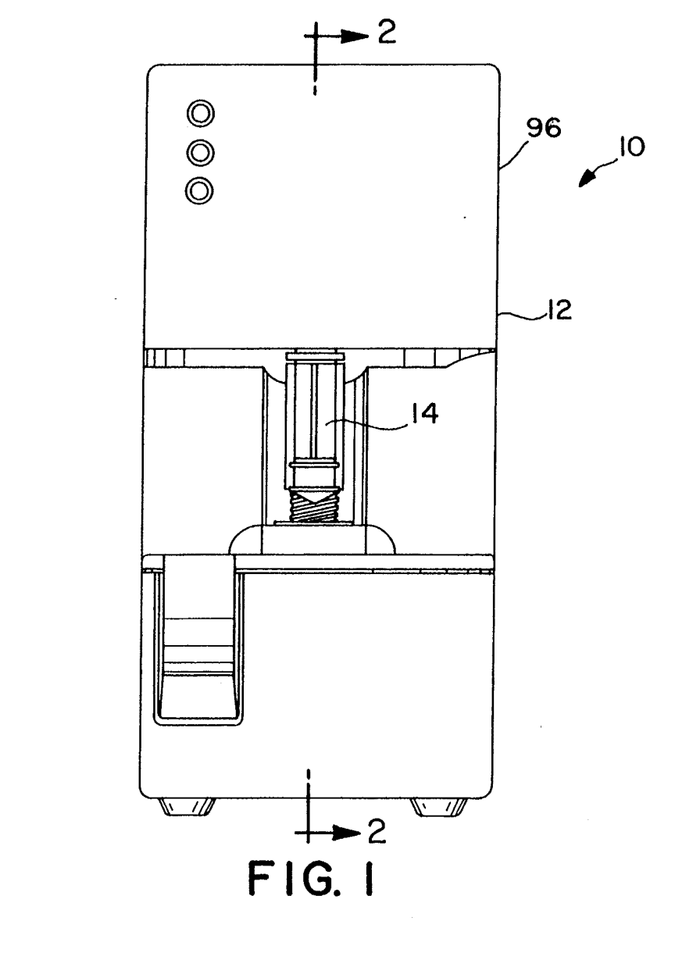
FIG. 1 is a front elevation view of a test analyser for the system of the invention.
Figure 2:
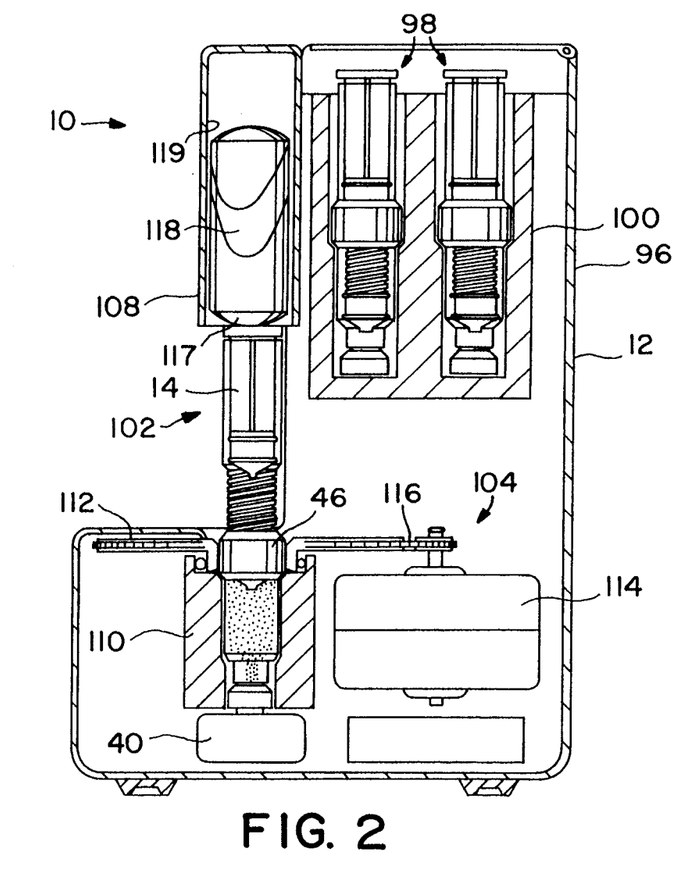
FIG. 2 is a section view of the test analyser taken along line 2—2 of FIG. 1.
Figure 3:
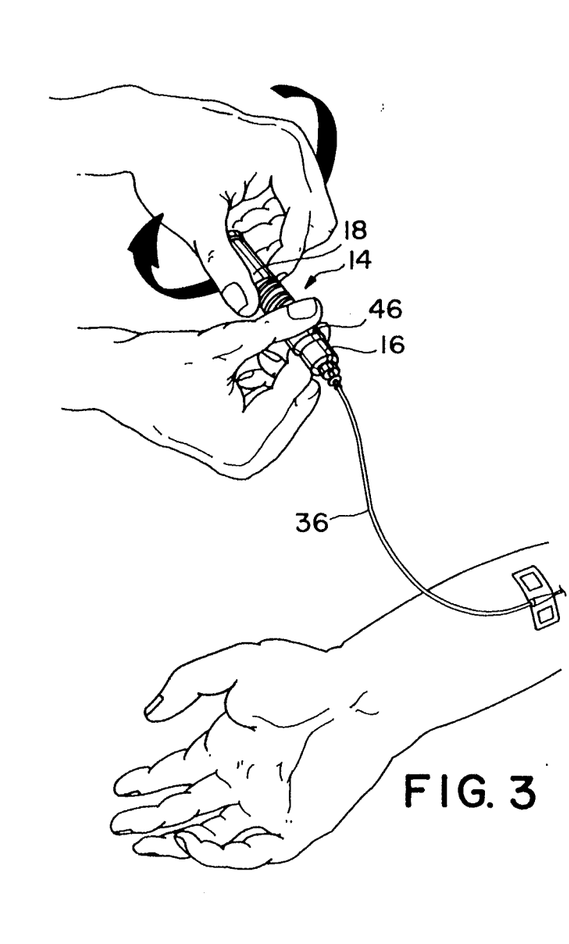
FIG. 3 is a schematic view of a technician collecting a blood specimen utilizing a cartridge according to the invention.

Referring to the drawing, a blood coagulation test system 10 according to the invention comprises a test analyser 12 and a syringe-like test cartridge 14. The test cartridge appears in upright position in FIGS. 4 and 5 while the cartridge is inverted when placed in the test analyser of FIGS. 1 and 2. Cartridge inversion is a matter of design choice of the analyser as testing can also be carried out with an upright cartridge.

The test cartridge is a syringe-type instrument of tubular form including an open ended collection chamber 16 fitted with a telescoping collection and storage plunger 18. A pressure piston 20 occupies a rear waste compartment 22 in the plunger for maintaining a counter pressure on a blood sample B being tested. The collection chamber 16 is generally tubular having a shoulder 24 defining the front wall of the chamber and having an inlet throat 26 through the front wall. A retaining collar 28 surrounds the throat forming therebetween an annular recess 30 for securing a variety of fittings over the open throat. As shown in the drawing, throat fittings include a pressure diaphragm cap 32, and a collection cap 34 having a captive intravenous tube 36 for collecting a blood sample. The pressure diaphragm cap includes a transverse diaphragm 38 for closing throat entry 39 and for transmitting blood pressure to pressure sensor 40. The cylindrical wall 42 of the collection chamber includes a circumferential flange 44 which engages and retains a driving sleeve 46 in operative position adjacent the open rear end 48 of the chamber.

Figure 4A:
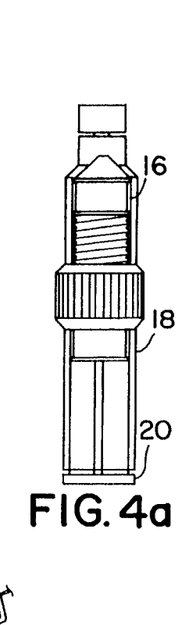
FIGS. 4a, b, and c are elevational views showing the external components of a test cartridge according to the invention (a) in pre-test configuration, (b) filled with a blood sample and ready for testing, and (c) ready for disposal after completion of a test.
Figure 4B:
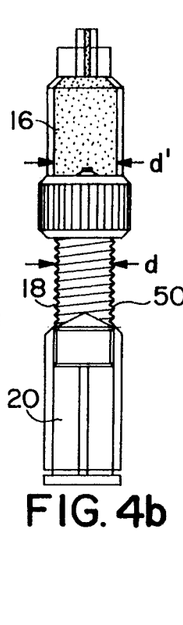
Figure 5A:
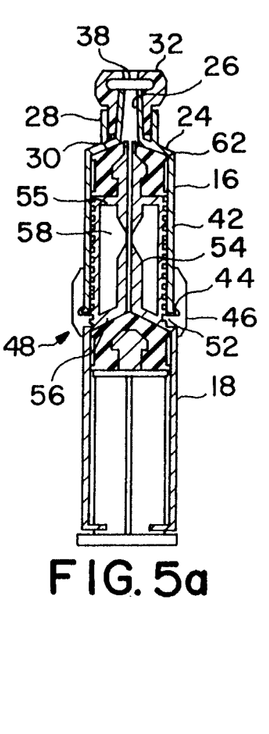
FIGS. 5a–e are elevational views in section respectively of test cartridges according to the invention (a) packaged for use, (b) drawing a blood sample, (c) in place in the test analyser and ready for test, (d) during a test, and (e) with test complete and cartridge ready for disposal.
Figure 5B:
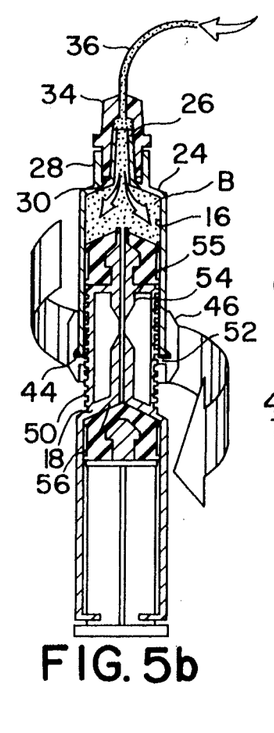
Figure 5C:
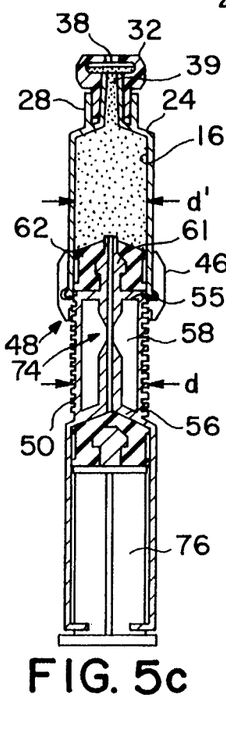
Figures 5D, 5E:
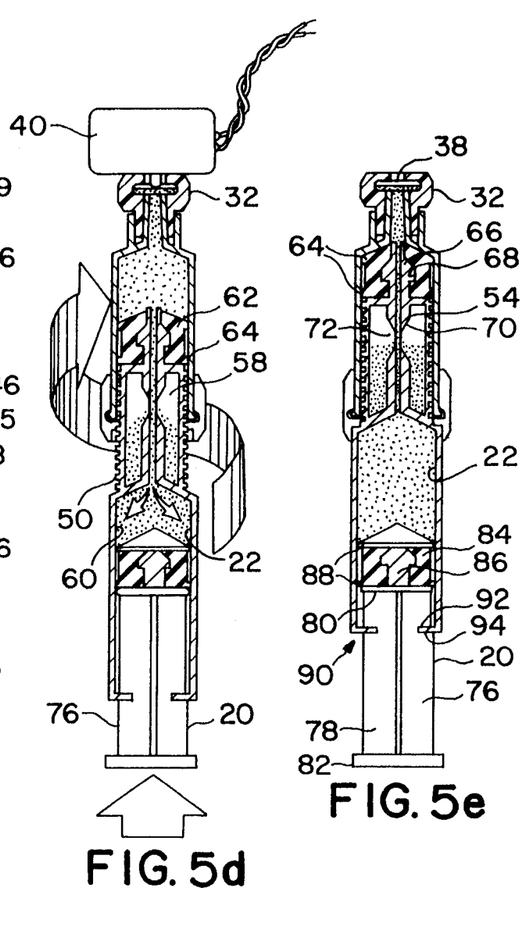

As shown in FIGS. 4b and 5c, the collection plunger 18 has a forward outer diameter d less than the inner chamber diameter d' for telescoping movement of the plunger into the collection chamber. The outer surface of the plunger has a screw thread 50 for engaging a corresponding thread 52 along the inner surface of the drive sleeve. Telescoping movement of chamber and plunger is achieved by turning the drive sleeve. Very precise linear movement of the plunger within the chamber is achieved by this screw drive arrangement. Consequently a blood sample may be drawn into the collection chamber and subsequently pushed into a capillary tube 54 at a steady flow rate so as to minimize blood turbulence and premature platelet activity.

The collection and storage plunger 18 is divided longitudinally by a lateral bulkhead 56 into a forward bleeding receptacle 58 and an aft waste compartment 60. The capillary tube 54 opens through the bulkhead and extends longitudinally forward through the bleeding receptacle and therebeyond through plunger front wall 55 opening into the sample collection chamber for conducting the blood sample through the cartridge. The tube structure can be formed integral with the bulkhead and with the front wall of the plunger. The front end 61 of the capillary tube projecting from the plunger 18 receives and positions a sealing band 62 within the collection chamber. Sealing rings 64 on the sealing band provide a fluid tight seal within the chamber as the plunger draws a blood sample and as it forces the sample through the capillary tube. The tube front end has an annular shoulder 66 nesting within a complementary recess 68 in the sealing band for securing the two together.

The section 70 of capillary tube located within the bleeding receptacle has a necked down wall portion 72 for location of a bleeding hole or aperture 74 (FIG. 5c) opening into the bleeding receptacle for determining hemostasis. The aperture is formed during manufacture of the test cartridge and its dimensions and contour are precisely controlled. For example, the tube outer diameter at the aperture may be approximately 1.00 mm, inner diameter approximately 0.50 mm, and aperture diameter approximately 0.15 mm. The tube wall surrounding the aperture is cleared of any wall fragments occurring as a result of hole formation so that hole dimensions and contour are standard for all test cartridges and do not influence platelet plug formation during blood tests.

The aft waste compartment 22 is occupied by telescoping pressure piston 20 slidably mounted therein for establishing a control pressure during testing. The piston comprises a cruciform support 76 formed of intersecting plates 78 terminating in discs 80, 82 at front and rear ends. A sealing band 84 is fitted to the front disc and retained thereon in axial alignment with the waste compartment by means of a mounting shoulder 86. The sealing band is provided with spaced sealing rings 88 for engaging and sealing the interior compartment wall in a fluid tight manner always confining waste blood to the compartment interior. The rear disc 82 of the pressure piston engages the counterpressure system as described below in detail. The pressure piston is guided by the open end 90 of the waste compartment in a suitable manner as, for example, by an inturned flange 92 with circumferentially spaced notches 94 engaging the piston plates 78. A primary purpose of the inturned flange is to prevent exit of the plunger from the waste compartment.

The test analyser 12 comprises basic components including or combinations of outer cabinet 96, test cartridge preheat cells 98, heater 100, test station 102, cartridge drive mechanism 104, pressure sensor 40, and cartridge counterpressure unit 108. The analyser may also include display screen, printer, and operating keyboard as integrated items (not illustrated) or as external items shared with other equipment.

A test cartridge is inverted for placement in the test analyser (FIGS. 1 and 2) with the blood sample chamber within heated chamber 110 for maintaining the sample at 37 deg. C. The pressure diaphragm cap engages the pressure sensor for detecting blood sample pressure changes occurring during sample test. The drive sleeve 46 engages a drive ring 112 which is driven by stepper motor 114 and drive belt 116 for precise load compensating control. The base of the cartridge contacts a counterpressure plate or surface 117 which applies a constant force of counterweight 118 to the pressure piston in the cartridge. The counterpressure plate forms part of the counterpressure unit which includes weight 118 movably supported in cell 119 for applying given force to the pressure piston. As a result, the piston exerts a constant force and pressure (60 mm Hg) on blood sample from the waste compartment through the capillary tube.

It will be noted that in a preferred embodiment of the invention, the diameters of the collection chamber and of the waste compartment are substantially the same so that forward movement of the plunger as shown in FIG. 5 (d) produces equal rearward movement of the pressure piston. The net result is the overall length of the cartridge remains approximately constant during a test. Compare FIGS. 5 (c), (d), and (e). The slight difference in overall length of the cartridge of FIGS. 5 (c) and (e) results from diversion of approximately 0.3 ml of blood sample into the bleeding receptacle during a test. This design of the cartridge simplifies design considerations of the counterpressure system.

In operation of the system, a technician begins with a test cartridge by removing and reserving the pressure diaphragm cap and by fitting the blood collection tube and cap or couple directly to a hypodermic needle. The operator manually rotates the drive sleeve to draw blood at a gradual and steady flow rate so as to avoid platelet activation. After the sample has been drawn, the collection tube and cap are removed and discarded and replaced by the pressure diaphragm cap which now remains permanently in place for testing and disposal of the cartridge. The cartridge is inserted into the test station engaging the pressure sensor, the drive ring and the counterpressure plate. Next the analyser begins the automated phase of the test following operator and preprogrammed software instructions. The drive ring rotates the drive sleeve in the direction of the arrow in FIG. 5d thereby establishing blood flow into the capillary tube at a constant flow rate. The pressure developed equals 60 mm Hg as flow begins and bleeding commences as the blood stream reaches the bleeding aperture in the capillary tube. Platelet plug formation gradually occurs filling the hole and causing a gradually increasing blood pressure within the cartridge. Blood pressure is monitored by the sensor and a trace of the pressure line is presented visually by the display screen and by the printer. See FIG. 6. When the test is completed, the cartridge is removed with the pressure diaphragm cap in tact and is discarded along with the collection tube. The test described provides evaluation of hemostasis of the sample.

Figure 6:
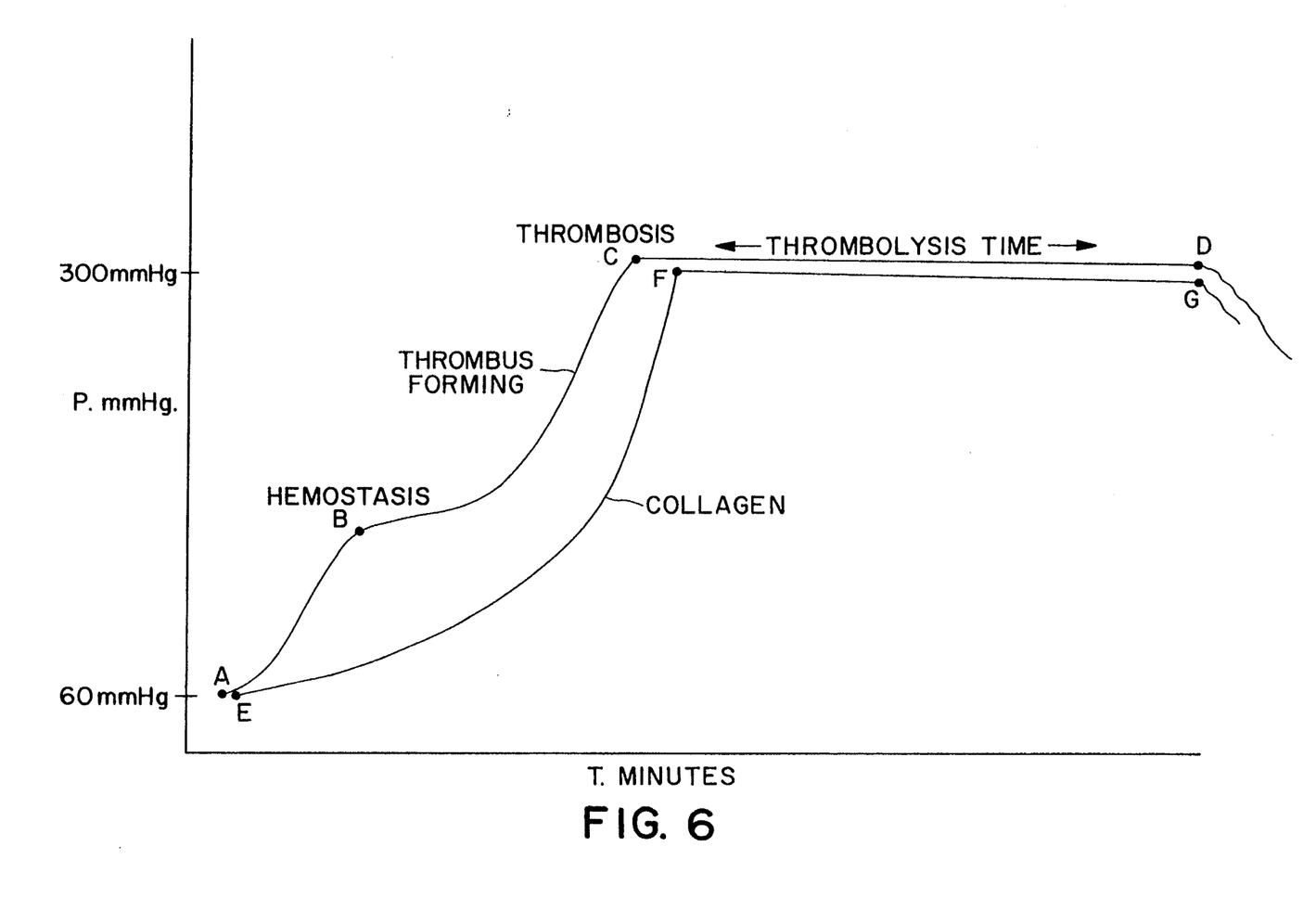
FIG. 6 is a graph presenting pressure/time traces of blood tests according to the invention.

The graph at FIG. 6 depicts pressure vs. time traces for various tests preformed and recorded by the test analyser. During a hemostasis test, the test cartridge and analyser establish flow of the blood sample into the capillary tube at an initial pressure of 60 mm Hg as indicated at point A in the graph. As bleeding continues, a platelet plug forms in the bleeding aperture causing a gradual rise in blood pressure within the cartridge which is monitored by the pressure sensor. Hemostasis occurs at point B with formation of the platelet plug completed and a steady blood pressure thereafter indicated by the analyser. Hemostasis time is recorded and may be directly noted by the technician.

With the same test cartridge in place, the analyser continues turning the drive sleeve maintaining blood flow through the capillary tube into the waste compartment. The flowing blood begins clotting (thrombus formation) in the capillary tube causing continued rise in blood pressure within the test cartridge which is recorded on the graph between points B and C. At point C thrombus formation is complete and the analyser records a cutoff pressure of approximately 300 mm Hg. Clotting time is directly noted on the graph.

In a typical test the elapsed time for hemostasis and occlusion (clotting) is about five to ten minutes with the exact time for each event being monitored and recorded by the analyser for each test sample.

The test cartridge remains in the analyser for thrombolysis evaluation. After thrombus formation (point C), the analyser through the drive motor maintains a given pressure of say 300 mm Hg on the blood sample within the cartridge. The analyser records thrombolysis time, i.e., the elapsed time between points C and D. The occurrence of thrombolysis is indicated by decrease in blood pressure beyond point D.

Figure 4C:
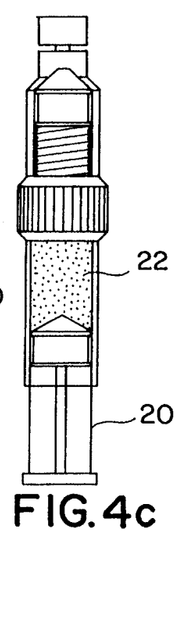
Figure 7:
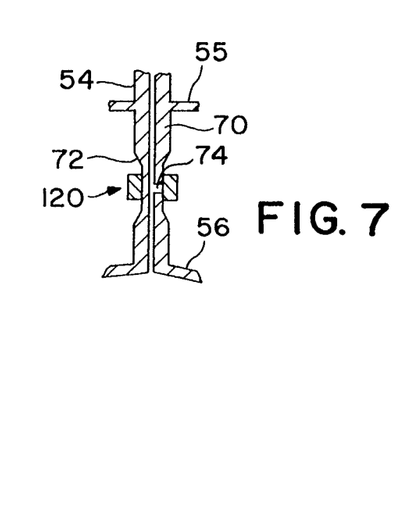
FIG. 7 is a fragmentary view of a test cartridge capillary tube fitted with a collagen disc for use in assessing collagen platelet interaction of a blood specimen.

FIG. 7 illustrates a modification to a test cartridge for assessing collagen platelet interaction. A test cartridge identical in all respects to the one described in connection with FIGS. 4 and 5, is modified by placing a collagen disc 120 around the capillary tube so as to cover the bleeding aperture thereby providing for blood collagen contact. In use, a blood sample is taken and the cartridge placed in the analyser as described. Blood flow is established within the capillary tube as the analyser monitors a rise in blood pressure from graph points E to F. At point F occlusion occurs and the time elapsed is noted and recorded by the analyser. Thrombolysis time for the blood sample is noted and recorded by the analyser between points F and G.

After each test is completed, the test cartridge is removed from the test analyser and discarded with the pressure diaphragm cap serving as a disposal cap for confining the blood sample in the cartridge.

The test cartridge and analyser can be used to monitor blood additives as for example heparin therapy by adding a fraction of a cc of the additive to a test cartridge and assessing modification of blood characteristics such as clotting time with various doses as recorded by the analyser.

The test cartridge and test analyser monitor and record blood pressure at a point upstream of the capillary tube by location and use of pressure monitoring components including pressure diaphragm cap and pressure sensor at the collection chamber inlet throat. In this way blood conditions being monitored, particularly clotting in the capillary tube, do not interfere with readings indicated by the analyser. The PCT patent apparatus identified above monitors blood pressure downstream of the bleeding puncture in the capillary tube and consequently does not "see" pressure changes in the tube after thrombus formation.

The test cartridge includes a flow circuit for the blood sample that is very short in comparison to the prior art thereby achieving complete test results with a low volume blood sample of about 2 ml.

The test cartridge and analyser provide in vitro blood analysis for hemostasis, clot formation, thrombolysis, and collagen platelet interaction reliably and repeatably immediately after sample collection under test conditions of constant temperature, pressure, and flow rate with minimal manipulation, agitation, and mechanical stress of the sample and with minimal disposal bulk. Once collected, the blood sample is confined to the test cartridge throughout testing and disposal thereby eliminating any opportunity for infecting personnel handling the cartridge in normal use. The system is particularly suited for use at patient sites and provides test results in a time period determined nearly entirely by the time required for collection of a sample and for occurrence of the blood functions being montored.

I claim:

1. A blood coagulation test system comprising a test cartridge and a test analyser for receiving the test cartridge and for executing a blood analysis protocol, the test cartridge having a cylinder defining a collection chamber, a first opening at one end of the cylinder for receiving a blood sample into the chamber, means for capping the first opening of the cylinder, a second opening at the other end of the cylinder, a plunger telescoped into the cylinder through the second opening for drawing a blood sample into the chamber through the first opening, the plunger being an elongate hollow tube having a bleeding receptacle and a waste compartment, a capillary tube extending through the plunger and forming a blood flow path from the collection chamber past the bleeding receptacle and into the waste compartment, a port in the capillary tube for bleeding the blood sample into the bleeding receptacle, means interconnecting the collection chamber and the plunger for moving the plunger at a steady rate for drawing a blood sample into the collection chamber and for expelling the sample from the chamber to establish blood flow through the capillary tube, a pressure piston forming part of the cartridge and being telescoped into the waste compartment and together with the waste compartment defining a waste chamber for receiving waste blood from the capillary tube, the pressure piston being adapted to apply a constant back pressure on blood in the waste chamber, the test analyser having means for maintaining the cartridge at constant temperature, means for driving the interconnecting means for telescoping the plunger into the collection chamber thereby expelling the blood sample therefrom and establishing blood flow through the capillary tube at a steady rate, means engaging the cartridge for sensing the pressure of blood flowing within the cartridge, means engaging the pressure piston for applying a back pressure on the blood in the waste chamber, and means for recording pressure variation of blood pressure within the cartridge while the blood sample flows through the capillary tube into the waste chamber.

2. A cartridge for blood coagulation tests comprising a cylinder defining a collection chamber, a first opening at one end of the cylinder for collecting a blood sample, a second opening through the other end of the cylinder, a plunger telescoped into the cylinder through the second opening for drawing a blood sample into the chamber, the plunger having a bleeding receptacle and a waste compartment having an interior wall, a capillary tube forming a blood flow path from the collection chamber past the bleeding receptacle and into the waste compartment, a port in the capillary tube for bleeding the blood sample into the bleeding receptacle, means interconnecting the collection chamber and the plunger for moving the plunger at a steady rate for drawing a blood sample into the collection chamber and for expelling the sample from the chamber to establish blood flow through the capillary tube, and means for applying a constant back pressure on blood in the waste compartment, so that blood flows through the capillary tube at a steady flow rate.

3. A cartridge as defined in claim 2 having a nozzle defining the first opening of the cylinder.

4. A cartridge as defined in claim 3 having a closure cap securing the nozzle.

5. A cartridge as defined in claim 3 having a collection cap and intravenous tube fitted to the nozzle.

6. A cartridge as defined in claim 3 having a pressure diaphragm closure fitted to the nozzle.

7. A cartridge as defined in claim 2 in which the plunger moving means includes a threaded exterior surface about the plunger and a threaded drive sleeve affixed to the cylinder near the second opening which is in driving engagement with the threaded surface of the plunger.

8. A cartridge as defined in claim 2 in which the back pressure means comprises a piston fitted into the waste compartment for defining the waste compartment and exerting a predetermined pressure on waste blood in the compartment.

9. A cartridge as defined in claim 8 in which the waste compartment and the collection chamber are substantially the same diameter so that forward movement of the plunger produces equal rearward movement of the piston and the overall length of the cartridge remains substantially constant as blood is expelled from the collection chamber into the capillary tube and waste compartment.

10. A cartridge as defined in claim 2 which further includes means for closing the first opening of the cylinder whereby the blood sample is entirely contained within the cartridge from collection to disposal of the cartridge at the conclusion of a test.

11. A cartridge as defined in claim 2 in which the capillary tube forms part of the plunger and has a front end extending into the collection chamber, and means fitted to the front end for providing a fluid tight seal within the chamber.

12. A cartridge as defined in claim 2 in which the constant back pressure means includes means for sealing the interior wall of the waste compartment in a fluid tight manner.

13. A cartridge as defined in claim 2 which includes a small amount of blood additive in the collection chamber for assessing modification to characteristics of a blood sample.

14. A cartridge as defined in claim 2 in which the blood flow path allows a low volume blood sample of about 2 ml to be analyzed thereby quickly achieving complete test results.

15. A test cartridge comprising a collection chamber having an inlet for receiving a blood sample, a plunger telescoped into the collection chamber for drawing a blood sample through the inlet into the chamber, a bleeding receptacle, a waste compartment, means defining a fluid path extending through the plunger and interconnecting the collection chamber, bleeding receptacle and waste compartment, the plunger being adapted to apply pressure to the blood sample in the collection chamber for establishing sample flow from the collection chamber through the fluid path to the waste compartment, a port in the fluid path for establishing bleeding of the sample into the bleeding receptacle, means for applying back pressure to the blood sample entering the waste compartment, and means for transmitting interior collection chamber blood pressure to the cartridge exterior.

16. A test cartridge as defined in claim 15 in which the means for transmitting interior collection chamber blood pressure also closes the collection chamber inlet.

17. A test cartridge as defined in claim 16 in which the means for closing the collection chamber inlet and transmitting interior collection chamber blood pressure comprises a pressure diaphragm closure cap applied to the chamber inlet.

18. A test cartridge as defined in claim 15 in which the fluid path, the bleeding receptacle, and the waste compartment form part of the plunger telescoping into the collection chamber.

19. A test cartridge as defined in claim 18 in which the part of the plunger telescoping into the collection chamber is provided with a screw thread and in which the collection chamber further comprises a threaded drive sleeve that interconnects with the screw thread on the plunger for enabling steady rate telescoping movement therebetween.

20. A test cartridge as defined in claim 15 in which the means for applying back pressure to the blood sample entering the waste compartment comprises a piston slidably mounted in the waste compartment for applying a given counterweight force and constant pressure to the blood sample.

21. A test cartridge as defined in claim 15 in which the port in the fluid path induces platelet plug formation in the port during bleeding of the blood sample into the bleeding receptacle thereby causing a gradual rise in sample blood pressure in the cartridge and providing an index of hemostasis of the blood sample.

22. A test cartridge as defined in claim 21 in which the fluid path induces thrombus formation thereby causing a further gradual rise in sample blood pressure in the cartridge providing an index of thrombosis of the blood sample.

23. A test cartridge as defined in claim 22 in which the means for applying back pressure to the blood sample entering the waste compartment maintains the blood pressure in the cartridge at a predetermined level after thrombosis occurs thereby providing an index of thrombolysis of the blood sample.

24. A test cartridge as defined in claim 15 which further includes collegen exposed to the blood sample through the port to provide an index of platelet collagen interaction by a measurement of rising blood pressure of the sample in the test cartridge.

25. A cartridge for blood coagulation tests comprising a cylinder defining a collection chamber, a first opening at one end of the cylinder for collecting a blood sample, a second opening through the other end of the cylinder, a plunger telescoped into the cylinder through the second opening for drawing a blood sample into the chamber, the plunger having a bleeding receptacle and a waste compartment, means defining a blood flow path from the collection chamber past the bleeding receptacle and into the waste compartment, and a port in the blood flow path for bleeding into the bleeding receptacle, wherein the plunger serves to expel the blood sample from the chamber to establish blood flow through the blood flow path.

26. A cartridge as defined in claim 25 in which the blood flow path for the blood sample from the collection chamber to the waste compartment allows a low volume blood sample of about 2 ml to be analyzed thereby quickly achieving complete test results.

27. A cartridge for blood coagulation tests comprising a cylinder defining a collection chamber, a first opening at one end of the cylinder for collecting a blood sample, a second opening through the other end of the cylinder, a plunger telescoped into the cylinder through the second opening for drawing a blood sample into the chamber, the plunger having a bleeding receptacle and a waste compartment, a capillary tube extending through the plunger and forming a blood flow path from the collection chamber past the bleeding receptacle and into the waste compartment, an aperture in the capillary tube for bleeding the blood sample into the bleeding receptacle, the aperture being formed during manufacture of the cartridge and having precise dimensions and contour, the plunger being adapted for drawing a blood sample into the collection chamber and for expelling the sample from the chamber to establish blood flow through the capillary tube and the aperture, and means for applying a constant back pressure on blood in the waste compartment, so that the blood flows through the capillary tube and the aperture at steady flow rates.

28. A cartridge for blood coagulation tests comprising a cylinder defining a collection chamber, a nozzle at one end of the cylinder for accommodating a fill connection for the flow of blood into the collection chamber, a second opening through the other end of the cylinder, a plunger telescoped into the cylinder through the second opening for drawing a blood sample into the chamber, the plunger being of tubular form and divided longitudinally by a lateral bulkhead into a bleeding receptacle and a waste compartment, the bleeding receptacle defined by a front plunger wall, a forward portion of the plunger, and the lateral bulkhead, the waste compartment defined by the lateral bulkhead, an aft portion of the plunger and an open read end, a capillary tube projecting forwardly from the front plunger wall into the collection chamber and extending through the plunger and forming a blood flow path from the collection chamber past the bleeding receptacle and into the waste compartment, a sealing ring about the forward projection of the capillary tube for forming a fluid tight seal with the collection chamber, an aperture in the capillary tube for bleeding the blood sample into the bleeding receptacle, the forward portion of the plunger having a threaded exterior surface, a drive ring rotatably affixed to the collection chamber near the second opening in engagement with the threaded exterior surface of the plunger for moving the plunger at a steady rate for drawing a blood sample into the collection chamber and for expelling the sample from the chamber to establish blood flow through the capillary tube, a pressure diaphragm closing the nozzle, a pressure piston telescoped into the waste compartment through the open end thereof for applying a constant back pressure on blood entering the waste compartment so that blood flows through the capillary tube at a steady flow rate, and a seal fitted to the pressure piston for forming a fluid tight seal between the piston and the waste compartment.

29. A test analyser for a test cartridge having a collection chamber for collecting a blood sample through a fill opening, a plunger telescoped into the collection chamber through a second opening for drawing a blood sample into the chamber, the plunger having a capillary tube extending therethrough and a waste compartment, a drive sleeve affixed to the collection chamber near the second opening and in driving engagement with the plunger to draw a blood sample into the collection chamber and to expel the sample from the chamber through the capillary tube and into the waste compartment, and a back pressure piston in the waste compartment, the analyser comprising means for maintaining the cartridge at constant temperature, means for engaging the drive sleeve affixed to the collection chamber for driving the plunger into the collection chamber thereby establishing blood flow through the capillary tube and into the waste compartment at a steady rate, means engaging the fill opening for sensing the pressure of blood flowing within the cartridge, means for applying a constant force on the back pressure piston for applying a back pressure on the blood flow entering the waste compartment, and means for recording pressure variation of blood pressure within the cartridge thereby providing an assessment of blood characteristics.

30. A test analyser as defined in claim 29 in which the means for maintaining the cartridge at constant temperature surrounds the the collection chamber.

31. A test analyser as defined in claim 29 which further includes a preheater for test cartridges.

32. A method of testing blood comprising the steps of drawing a blood sample from a patient through a nozzle into a cylinder by a first stroke of a piston telescoped into the cylinder, closing the nozzle with a cap, applying pressure to the blood sample in the cylinder by a return stroke of the piston into the cylinder thereby establishing flow of the blood sample from the cylinder through a capillary tube having a standard preformed aperture and into a waste compartment both formed within the piston, applying a constant back pressure on the blood sample in the waste compartment to maintain the flow through the capillary tube at an established control pressure, diverting a portion of pressurized blood sample flow from the capillary tube through the aperture, and determining one or more blood characteristics by observing variation in blood pressure within the cylinder.

33. A method as defined in claim 32 which further includes the step of maintaining the temperature of the blood sample at 37 deg. C. for each step of the method and in which the established control pressure is 60 mm Hg.

34. A method as defined in claim 32 which further includes the step of preheating the cylinder, piston, capillary tube, and waste compartment to a temperature of 37 degrees centigrade before drawing a blood sample from a patient.

35. A method as defined in claim 32 in which blood characteristics for hemostasis, thrombus, and thrombolysis are sequentially determined.

36. A method as defined in claim 32 which further includes the step of placing collagen at the aperture for assessing collagen platelet interaction of the blood sample.

* * * * *